United States Patent [19]

Groves et al.

[11] Patent Number: 4,822,899
[45] Date of Patent: Apr. 18, 1989

[54] METALLIC PORPHYRIN COMPLEXES AS CATALYSTS IN EPOXIDATION REACTIONS

[75] Inventors: John T. Groves; Robert Quinn, both of Ann Arbor, Mich.

[73] Assignee: The University of Michigan, Ann Arbor, Mich.

[21] Appl. No.: 722,956

[22] Filed: Apr. 12, 1985

[51] Int. Cl.$^4$ ................. C07D 301/03; C07D 301/04; C07D 301/06
[52] U.S. Cl. .................................... 549/533; 540/145
[58] Field of Search .......................................... 549/533

[56] References Cited

PUBLICATIONS

Groves et al., JACS, vol. 107, (1985), pp. 5790–5792.
I. Tabushi et al., Jour. Am. Chem. Soc., (1981), 103, pp. 7371–7373.
H. J. Ledon et al., Jour. Am. Chem. Soc., (1981), 103, pp. 3601–3603.
De Carvalho et al., Tetrahedron Letters, vol. 24(34), (1983), pp. 3621–3624.
D. Mansuy et al., Jour. Chem. Soc., Chem. Comm., (1983), No. 6, pp. 253–254.
D. Dolphin et al., Inorganica Chimica Acta, 79, (1983), pp. 25–27.
J. R. Lindsay Smith et al., J. Chem. Soc. Perkin Trans. II, (1982), pp. 1009–1015.
John T,. Groves et al., Jour. Am. Chem. Soc., (1978), 101, pp. 1032–1033.
John T. Groves et al., Jour. Am. Chem. Soc., (1980), 102, pp. 6377–6380.
John T. Groves et al., Jour. Am. Chem. Soc., (1981), 103, pp. 2884–2886.

*Primary Examiner*—Richard L. Raymond
*Attorney, Agent, or Firm*—Paul D. Hayhurst

[57] ABSTRACT

Metallic porphyrin complexes are useful as catalysts for the epoxidation of olefins at ambient temperature and pressure using oxygen, which preferably is supplied either as air or pure oxygen, without need for a coreductant.

19 Claims, No Drawings

METALLIC PORPHYRIN COMPLEXES AS CATALYSTS IN EPOXIDATION REACTIONS

BACKGROUND OF THE INVENTION

The present invention relates to metallic porphyrin complexes and their use as catalysts for the oxidation of hydrocarbons.

Epoxides, and other compounds having an oxirane ring such as ethylene oxide, propylene oxide, epoxidized fatty acids and the like, are conventionally produced by indirect means from the corresponding monoolefinically unsaturated compounds. For example, oxirane compounds typically are prepared by reaction of an olefin with chlorine in alkaline medium (forming, e.g., epichlorohydrin) followed by reaction with base; reaction of an olefin with an organic hydroperoxide employing a Group V, VI or VII metal catalyst; or reaction of an olefin with a peracid (e.g., peracetic or perbenzoic acid). U.S. Pat. No. 4,356,311 discloses the epoxidation of olefins using a transition metal nitro complex and a thallium (III) compound, such as a thallium (III) carboxylate, as an "olefin activator" or cocatalyst.

Interest in hydrocarbon oxidation has stimulated a major effort to model the oxygen activation and transfer reactions characteristic of cytochrome P-450. See, F. P. Guengerich et al., *Acc. Chem. Res.*, 17, pp. 9–16 (1984); R. E. White et al., *Ann. Rev. Biochem.*, 49, pp. 315–356 (1980); V. Ullrich, *Trop. Curr. Chem.*, 83, pp. 67–104 (1979); J. T. Groves, *Adv. Inorg. Biochem.*, pp. 119–145 (1979); J. T. Groves et al., *J. Am. chem. Soc.*, 101, pp. 1032–1033 (1979); J. T. Groves et al., *J. Am. Chem. Soc.*, 102, pp. 6375 et seq., (1980); J. T. Groves et al., *J. Am. Chem. Soc.*, 105, pp. 5786–5791 (1983); C. K. Chang et al., *J. Am. Chem. Soc.*, 101, pp. 3413–3415 (1979); J. R. Lindsay Smith et al., *J. Chem. Soc., Perkin Trans.* 2, pp. 1009–1015 (1982); D. Dolphin et al., *Inorg. Chim. Acta*, 79, pp. 25–27 (1983); D. Mansuy et al., *J. Chem. Soc., Chem. Commun.*, pp. 253–254 (1983); C. L. Hill et al., *J. Org. Chem.*, 48, pp. 3277–3281 (1983); I. Tabushi et al., *J. Am. Chem. Soc.*, 103, pp. 7371–7373 (1981); J. J. Ledon et al., *J. Am. Chem. Soc.*, 103, pp. 3601–3603 (1981); M. W. Nee et al., *J. Am. Chem. Soc.*, 104, pp. 6123–6125 (1982); and M.-E. De Carvalho et al., *Tetrahedron Lett.*, 24, pp. 3621–3624 (1983). Model and enzymic studies have implicated the intermediacy of an oxoiron intermediate in the probable catalytic cycle. See, J. T. Groves et al., *J. Am. Chem. Soc.*, 96, p. 5274 (1974); J. T. Groves et al., *J. Am. Chem. Soc.*, 103, pp. 2884–2886 (1981); B. Boso et al., *J. Chem. Phys.*, 79, pp. 1122–1126 (1983); F. Lichtenbérger et al., *Biochem. Biophys. Res. Commun.*, 70, pp. 939–946 (1976); and K. B. Sharpless et al., *J. Am. Chem. Soc.*, 93, pp. 2316–2318 (1971). The stoichiometry of the reaction requires two electrons from an exogenous source. Thus, most of the model systems have employed peroxidic oxidants such as iodosylbenzene or hypochlorite. The reductive activation of dioxygen has been reported in several cases, but each requires the consumption of at least stoichiometric amounts of a reducing agent. See D. Mansuy et al., supra and I. Tabushi et al., supra. Clearly, the development of a practical catalyst for the epoxidation of hydrocarbons must achieve access to the reactive oxometal species without the need for a coreductant. We describe here the first such system.

SUMMARY OF THE INVENTION

The present invention is such a process for the epoxidation of olefins, and comprises contacting an olefin with oxygen in the presence of a catalytic amount of a metallic porphyrin complex under reaction conditions such that the olefin is at least partially epoxidized. Novel metallic porphyrin complexes are another aspect of the presetn invention. Surprisingly, the process of the present invention provides for the ready aerobic epoxidation of olefins at ambient conditions, i.e., at room temperature and pressure using air. Unexpectedly, the process does not require a sacrificial reducing agent, or additional coparticipants, activators or cocatalysts, such as thallium (III), or iodosylbenzene. The use of sacrifical reducing agents leads to by-product formation, such as the formation of $H_2O$ and CO. The use of cocatalysts, etc., results in additional expense for raw materials, processing, separations, and the like. These disadvantages are obviated by the process of the present invention.

DETAILED DESCRIPTION OF THE INVENTION

The process of the present invention requires an olefin, an oxidizing agent, and a catalyst. The olefin can be aromatic, aliphatic, mixed aromatic-aliphatic, cyclic, branched- or straight-chain, or combinations thereof. Examples of preferred olefins include 1-octene, cyclooctene, styrene, $\beta$-methylstyrene, norbornene and propylene. Mixtures of olefins can be employed. The olefin optionally can be substituted with moieties which do not prevent epoxidation, and which can contain atoms other than carbon and hydrogen. Examples of such substituent moieties include, for example, halogens and the substituent moieties mentioned in U.S. Pat. No. 4,356,311, the relevant teaching of which is incorporated herein by reference.

The oxidizing agent can be anything which is a source of oxygen under reaction conditions. Oxygen is the preferred oxidizing agent. The oxygen can be supplied as air, commercially pure oxygen, or air enriched with oxygen. For the sake of convenience, air is the preferred oxidizing agent. Advantageously, a gaseous diluent is included in the oxygen component fed to the reactor. Examples of typical diluents include carbon dioxide, nitrogen, noble gases, and steam, either individually or as mixtures. The diluent can be employed in any amount at which the reaction will proceed. Preferably, from about zero to about 10 moles of diluent is employed per mole of oxygen fed to the reactor. The oxygen is supplied in an amount which is sufficient to allow the reaction to proceed. Typically, from about 0.1 to about 40 or more moles of oxygen is employed per mole of olefinic double bond. The use of less than stoichiometric quantities of oxygen leads to incomplete reaction. Preferably, from about 0.5 to abouyt 15 moles of molecular oxygen is employed per mole of olefinic double bond. Known precautions should be taken when feeding explosive mixtures of the olefin and oxygen into the reactor.

The catalyst of the present invention is a metallic porphyrin complex of the formula $M(L_4)(X)_2$ wherein $L_4$ is any combination of monodentate, bidentate, tridentate, and tetradentate ligands such as to provide four bonding sites; wherein X is O or a weakly coordinating ligand, such as tetrahydrofuran or acetonitrile; and wherein the metal, M, is niobium, rhenium, ruthenium, osmium, rhodium or iridium. The ligand, $L_4$, is a ligand which can form a dioxo complex which can catalytically epoxidize olefins. Preferred catalysts are represented generally by the formula:

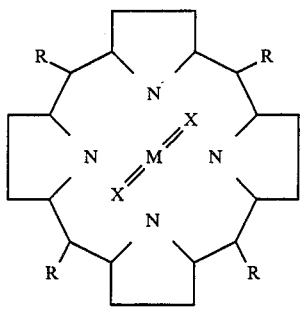

wherein M is as defined previously, X is O, and each R independently is an aromatic moiety having sufficient size to prevent formation of the dimer of the complex, i.e., a dimer linked by replacement of one of the X moieties shown in the preceding formula. Preferably, R is an ortho-disubstituted phenyl moiety represented by the formula:

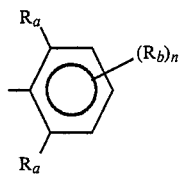

wherein n is from zero to 3, and each $R_a$ and $R_b$ is independently aryl, haloaryl, alkaryl, haloalkaryl, aralkyl, haloaralkyl, alkyl, halo or haloalkyl. Preferably, M is ruthenium, $R_a$ is lower alkyl of from 1 to about 4 carbon atoms, and the oxygen atoms are trans. More preferably, each $R_a$ is methyl, M is Ru (VI), n is 1, and $R_b$ is methyl in the para position. The preparation of a trans-dioxoruthenium (VI) complex is described in *Inorganic Chemistry*, V. 23, pp. 3844-6 (1984) and is incorporated herein by reference.

The catalyst is employed in a catalytic amount. Typically, the catalyst is present at a minimum catalyst to olefin ratio of at least about 0.0025 mole of catalyst per mole of olefinic double bond, and preferably at least about 0.2 mole of catalyst per mole of olefinic double bond. These ratios are typical, with the actual ratios being determined by the specific catalyst and hydrocarbon employed as well as practical considerations such as convenience and economy. The catalyst can be employed on a support.

The process of the present invention can be conducted under any combination of temperatures and pressure at which the reaction will proceed, although high temperature can cause catalyst decomposition. Typically, the reaction is conducted at from about 0° C. to about 100° C., and preferably at from about 15° C. to about 50° C. The reaction can be conducted at sub- or superatomspheric pressures. Typically, a pressure of from about 0.5 atm (50 kPa) to about 4 atm (400 kPa) is employed. The most preferred temperature is ambient temperature and the most preferred pressure is ambient pressure.

A solvent is optionally employed in the process of the present invention. The solvent serves to dissolve the catalyst and the olefin, and can be chosen from a wide variety of compounds which allow the epoxidation reaction to proceed. Examples of typical solvents include aromatic hydrocarbons, such as benzene, chlorobenzene, toluene, xylenes, and the like; halogenated alkanes, such as methylene chloride; and excess olefin. Benzene is the preferred solvent. The amount of solvent employed can vary widely. Typically, from about 0.001 to about 1 liter of solvent is employed per mole of olefin, preferably from about 0.005 to about 0.05.

SPECIFIC EMBODIMENTS

The following examples are given to illustrate the invention and should not be construed as limiting its scope. All parts and percentages are by weight unless otherwise indicated.

Preparation 1

Tetramesitylporphyrinato ruthenium (II) carbonyl [RuTMP(CO)]

RuTMP(CO) is prepared by refluxing 0.5 g of tetramesitylporphyrin with 0.5 g of $Ru_3(CO)_{12}$ in 200 ml decalin for 48 hours. Following column chromatography (alumina, dichloromethane, chloroform), pure RuTMP(CO) is obtained by recrystallization from benzene/acetonitrile.

Tetramesitylporphyrin is prepared with reference to the literature method described in *Aust. J. Chem.*, 17, pp. 1028-1035 (1964) as modified as described in *J.A.C.S.* 105 pp. 6243-8 (1983).

Example 1

Preparation of Dioxo[5,10,15,20-tetrakis(2,4,6-trimethylphenyl)-21H,23H-porphinato(2-)-N21,N22,N23,N24]-ruthenium $RuTMP(O)_2$, the title compound, is prepared by stirring 0.1 g of tetramesitylporphyrinato ruthenium (II) carbonyl, RuTMP(CO), in 20 ml of dichloromethane with 0.04 g of meta-chloroperoxybenzoic acid for 1 hour. The solvent is removed under vacuum. The remaining solid is dissolved in benzene and the solution is chromatographed on basic alumina. The isolated solid is recrystallized from benzene/acetonitrile.

Examples 2-8

Approximately 2 micromoles ($\pm 0.5$ $\mu$mole) of the product complex of Example 1, dioxo(tetramesitylporphyrinato)-ruthenium (VI) (hereinafter $Ru(TMP)(O)_2$), are dissolved in 200 $\mu$l of benzene to form a catalyst solution. A quantity of an olefin or mixture of olefins is then added to the solution at about 25° C. and ambient pressure to form a reaction solution. The solution is added to a cylindrical glass vessel having a volume of approximately 2 ml, then the reaction atmosphere is purged with commercially pure oxygen. The reaction solution is stirred for about 24 hours. The results are listed in the following table:

| | | Equivalent Epoxide[a] | | | |
|---|---|---|---|---|---|
| Ex. | Substrate | simc | c-o | t-o | n.o. |
| 2 | cyclooctene | 0.5 | 26[b] | — | — |
| 3 | cis-2-methylstyrene | 0.5 | 32.7 | 1.5 | — |
| 4 | trans-2-methylstyrene | 0.5 | 0.1 | 16.2 | — |
| 5 | norbornene | 0.44 | — | — | 43.2[c] |
| 6 | cis-2-methylstyrene | 0.4 | 28.6 | 2.0 | — |
|   | trans-2-methylstyrene | 0.4 | | | |
| 7 | cis-2-methylstyrene | 0.5 | 7.3 | 0.4 | 22.6 |

-continued

| Ex. | Substrate | Equivalent Epoxide[a] | | | |
|---|---|---|---|---|---|
| | | simc | c-o | t-o | n.o. |
| | norbornene | 0.5 | | | |
| 8 | trans-2-methylstyrene | 0.44 | — | 0.6 | 45.6[c] |
| | norbornene | 0.44 | | | | simc = substrate initial molar concentration
c-o = cis-oxide
t-o = trans-oxide
n.o. = norbornene oxide
[a]equivalents of epoxide based on catalyst
[b]cyclooctene oxide
[c]simultaneous runs with a separate batch of catalyst No other products or by-products, such as $H_2O$ or CO, are observed.

Example 9

Anerobic Oxidation of Olefin

Approximately 2 micromoles of $RuTMP(O)_2$ is dissolved in 200 μl of degassed benzene under an inert atmosphere. A quantity of cyclooctene is then added to the solution at about 25° C. The concentration of cyclooctene in the reaction mixture is 0.1 molar. The reaction solution is stirred for about 24 hours. One equivalent of cyclooctene oxide is produced, based on equivalents of $RuTMP(O)_2$ present.

Example 9 demonstrates an anerobic epoxidation process which can be employed in the epoxidation of olefins which could be unstable or potentially unstable in an atmosphere of, e.g., air or oxygen. The complex can be regenerated by exposing it to oxygen, and the cycle could be repeated as desired.

What is claimed is:

1. A process for the epoxidation of olefins, the process comprising contacting an olefin with a catalytic amount of a metallic porphyrin complex wherein the metal is Ru, Os, Rh, Ir, Nb or Re, in the substantial absence of coreductants and peroxidic oxidants under reaction conditions such that an epoxide of the olefin is formed.

2. The process of claim 1 wherein the complex is a ruthenium porphyrin complex.

3. The process of claim 1 wherein the olefin is ethylene, propylene or butylene.

4. The process of claim 1 wherein the complex is represented by the formula:

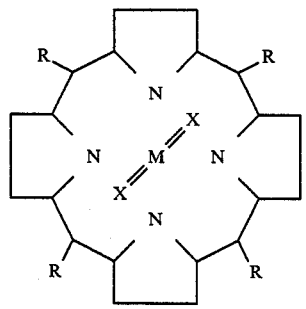

wherein the metal is represented by M, X is O or a weakly coordinating ligand, and wherein each R independently is an aromatic moiety having sufficient size to prevent formation of a dimer complex.

5. The process of claim 4 wherein the contacting is conducted in the presence of oxygen.

6. The process of claim 4 wherein the contacting is conducted at ambient pressure.

7. The process of claim 4 wherein the temperature is ambient.

8. The process of claim 4 wherein the oxygen is supplied as air.

9. The process of claim 4 wherein the contacting occurs in the presence of a solvent.

10. A process for the epoxidation of olefins comprising contacting under reaction conditions an olefin with oxygen and a catalytic amount of a catalyst represented generally by the formula:

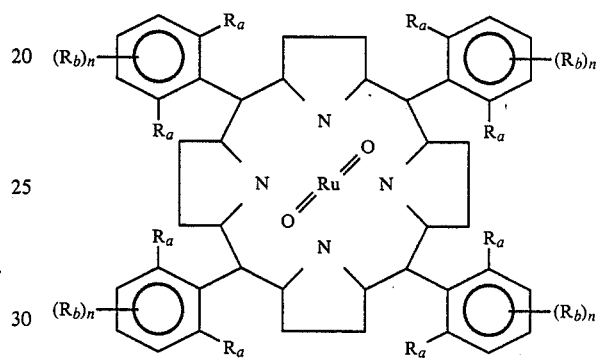

wherein each $R_a$ and $R_b$ independently is aryl, haloaryl, alkyl, halo, haloalkyl, haloalkaryl, aralkyl, alkaryl or haloaralkyl; and each n independently is from zero to 3.

11. The process of claim 10 conducted in the substantial absence of a coreductant.

12. The process of claim 10 wherein the contacting is at ambient temperature and pressure.

13. The process of claim 10 wherein the oxygen is supplied as air.

14. The process of claim 10 conducted in the presence of a solvent, the solvent comprising a solvent selected from the group consisting of benzene, toluene, xylene, chlorobenzene or methylene chloride.

15. The process of claim 10 wherein the oxygen atoms are trans, and each $R_a$ independently is lower alkyl of from about 1 to about 4 carbon atoms.

16. The process of claim 15 wherein n is 1 and each $R_b$ is methyl in the para position.

17. The process of claim 15 wherein each $R_b$ is methyl.

18. The process of claim 10 wherein the olefin is ethylene, propylene or butylene.

19. An aerobic process for the selective epoxidation of olefins, the process comprising contacting an olefin with air at about ambient temperature and pressure in the presence of dioxo[5,10,15,20-tetrakis(2,4,6-trimethylphenyl)-21H,23H-porphinato(2-)-N21,N22,N23,N24]-ruthenium and in the substantial absence of a peroxidic oxidant under reaction conditions such that an epoxide of the olefin is formed.

* * * * *